United States Patent
Weber et al.

(10) Patent No.: US 10,786,756 B2
(45) Date of Patent: Sep. 29, 2020

(54) SIMULATED MOVING BED SEPARATION PROCESS

(71) Applicants: EXXONMOBIL CHEMICAL PATENTS INC., Baytown, TX (US); GEORGIA TECH RESEARCH CORPORATION, Atlanta, GA (US)

(72) Inventors: Michael W. Weber, Houston, TX (US); Siwei Guo, Atlanta, GA (US); Yoshiaki Kawajiri, Nagoya (JP); Jason Bentley, Duluth, GA (US); Gaurav Agrawal, Houston, TX (US); Michael Salciccioli, Houston, TN (US); Dana L. Pilliod, League City, TX (US)

(73) Assignees: EXXONMOBIL CHEMICAL PATENTS INC., Baytown, TX (US); GEORGIA TECH RESEARCH CORPORATION, Atlanta, GA (US)

( * ) Notice: Subject to any disclaimer, the term of this patent is extended or adjusted under 35 U.S.C. 154(b) by 204 days.

(21) Appl. No.: 16/074,338

(22) PCT Filed: Feb. 9, 2017

(86) PCT No.: PCT/US2017/017209
§ 371 (c)(1),
(2) Date: Jul. 31, 2018

(87) PCT Pub. No.: WO2017/155664
PCT Pub. Date: Sep. 14, 2017

(65) Prior Publication Data
US 2019/0184311 A1    Jun. 20, 2019

Related U.S. Application Data

(60) Provisional application No. 62/307,044, filed on Mar. 11, 2016.

(51) Int. Cl.
*B01D 15/18* (2006.01)
*C07C 7/12* (2006.01)
(Continued)

(52) U.S. Cl.
CPC ....... *B01D 15/1828* (2013.01); *B01D 15/185* (2013.01); *C07C 7/12* (2013.01);
(Continued)

(58) Field of Classification Search
CPC .............. B01D 15/1828; B01D 15/185; B01D 2215/023; B01D 2259/40004; C07C 7/12; C07C 15/08; C07C 15/073
See application file for complete search history.

(56) References Cited

U.S. PATENT DOCUMENTS 3,201,491 A    8/1965   Stine et al.
4,029,717 A    6/1977   Healy et al.
(Continued)

FOREIGN PATENT DOCUMENTS

WO    2016/133589 A1    8/2016

OTHER PUBLICATIONS

International Search Report and Written Opinion issued in the corresponding application No. PCT/US2017/017209 dated May 11, 2017.
(Continued)

*Primary Examiner* — Benjamin L Lebron
(74) *Attorney, Agent, or Firm* — Roberts Calderon Safran & Cole P.C.

(57) ABSTRACT

The process involves the use of two rotary valves to implement Varicol operation of a simulated moving bed apparatus to separate a product from at least one multicomponent feed. In a particular embodiment, paraxylene is separated from a mixture of C8 aromatic hydrocarbons. The use of the Varicol process further enhances the separation of the desired prod-
(Continued)

uct and provides flexibility with a simulated moving bed apparatus using dual rotary valves.

20 Claims, 4 Drawing Sheets

(51) Int. Cl.
*C07C 15/08* (2006.01)
*C07C 15/073* (2006.01)
(52) U.S. Cl.
CPC ........ *C07C 15/08* (2013.01); *B01D 2215/023* (2013.01); *B01D 2259/40005* (2013.01); *C07C 15/073* (2013.01)

(56) References Cited

U.S. PATENT DOCUMENTS

| | | |
|---|---|---|
| 5,102,553 A | 4/1992 | Kearney et al. |
| 6,136,198 A | 10/2000 | Adam et al. |
| 8,168,845 B2 | 5/2012 | Porter et al. |
| 2009/0234170 A1 | 9/2009 | Lee et al. |
| 2010/0125163 A1 | 5/2010 | Porter et al. |
| 2013/0053610 A1 | 2/2013 | Leinekugel Le Cocq et al. |
| 2016/0145174 A1 | 5/2016 | Porter et al. |

OTHER PUBLICATIONS

Kawajiri et al., "Optimization strategies for simulated moving bed and PowerFeed processes", AIChE J. vol. 52 (2006) 8, pp. 1343-1350.

Zhang et al., "PowerFeed operation of simulated moving bed units: changing flow-rates during the switching interval", Journal of Chromatography A. 1006, pp. 87-99, 2003, Elsevier B.V.

SIMULATED MOVING BED SEPARATION PROCESS

CROSS-REFERENCE TO RELATED APPLICATIONS

The present application is a U.S. National Phase of PCT/US2017/017209 filed on Feb. 9, 2017 claiming priority to provisional U.S. Patent application No. 62/307,044 filed Mar. 11, 2016. The disclosure of the PCT Application is hereby incorporated by reference into the present Application.

FIELD OF THE INVENTION

The invention relates to a process for separating product from at least one multicomponent feed by means of a simulated moving bed apparatus. The process involves the use of two rotary valves to implement Varicol operation of the simulated moving bed apparatus.

BACKGROUND OF THE INVENTION

Simulated moving bed separation may be used to separate one or more components of multicomponent mixtures, where the components have similar boiling points. Such multicomponent mixtures include mixtures of organic compounds, which are manufactured in the sugar, petrochemical, and pharmaceutical industries. Simulated moving bed separation is especially useful for separating paraxylene from a mixture of $C_8$ aromatics (i.e. aromatic compounds having 8 carbon atoms). Of the $C_8$ isomers, paraxylene is the most commercially valuable. A commercial embodiment of a simulated moving bed adsorption apparatus, which is used to recover paraxylene from a mixture of $C_8$ aromatics, is the well-known Parex™ process. See by way of example U.S. Pat. Nos. 3,201,491; 3,761,533; and 4,029,717.

In a Parex™ unit, the locations of liquid input and output are moved by a fluid directing device described herein as a rotary valve device. This device may comprise one or more rotary valves, as well as various control and accessory means, such as inlet conduits, outlets conduits, and valves associated therewith. The rotary valve device works in conjunction with conduits in fluid communication with adsorbent beds. The rotary valve device accomplishes moving the input and output locations through first directing the liquid introduction or withdrawal conduits to specific conduits in fluid communication with particular adsorbent beds. After a specified time period, called the step time, the rotary valve device advances one index and redirects the liquid inputs and outputs to the conduit immediately adjacent and downstream of the previously used conduits. Each advancement of the rotary valve device to a new position is generally called a valve step, and the completion of all the valve steps is called a valve cycle. The step time or step time interval is uniform for each valve step in a valve cycle, and may be from about 30 seconds to 4 minutes.

An example of a commercial simulated moving bed adsorption apparatus contains 24 adsorbent beds and 24 conduits individually connected to a bed and providing fluid communication with the rotary valve device. The conduits of the adsorption apparatus may function, over time, as at least two liquid input conduits (e.g., a feed input conduit and a desorbent input conduit) and two liquid output conduits (e.g., an extract withdrawal conduit and a reformate withdrawal conduit).

In some simulated moving bed systems, a second rotary valve is used in parallel to allow for extra capacity or improve continuity of operations. A system with two rotary valves is described in U.S. Pat. No. 8,168,845.

In standard simulated moving-bed separation processes, the flow rate of streams into and out of the simulated moving bed are held constant during the step time. However, modulation of flow during the step time has been found to enhance separation in certain instances involving simulated moving bed separation of fructose and glucose or separation of 1,1'-bi-2-naphthol enatiomers. The enhanced separation may result in greater purity of product streams or less desorbent use. This process for modulating flow rates during a step time has been referred to as a PowerFeed process. Examples of PowerFeed processes are described in an article by Kawajiri et al., "Optimization strategies for simulated moving bed and PowerFeed processes", AIChE J. Vol. 52 (2006) B, pp. 1343-1350, and in an article by Zhang et al., "PowerFeed operation of simulated moving bed units: changing flow-rates during the switching interval", Journal of Chromatography A. 1006, pp. 87-99, 2003, Elsevier B.V. Systems utilizing PowerFeed for the separation of $C_8$ aromatics are described in International Patent Application No. PCT/US2015/06701.

Varicol is an operational technique for simulated moving bed applications in which the locations of the feeds and outlets are shifted asymmetrically, i.e., not simultaneously. This operational technique is described in U.S. Pat. No. 6,136,198. The ability to move the stream locations at different times allows for extra flexibility in optimizing the operation of the simulated moving bed. However, the use of a multi-port switching valve to simultaneously shift the stream positions limits the use of this technique in rotary valve systems and limits the efficiency of the system.

It is desirable to adapt the above-described techniques to a simulated moving bed system using rotary valves to further increase the optimization and efficiency of the separation.

SUMMARY OF THE INVENTION

The present invention is directed to the separation of a product from at least one multicomponent feed, in particular the separation of paraxylene from a mixture of $C_8$ aromatic hydrocarbons, by a simulated moving bed process with two rotary valves mimicking the asymmetric changing of flows of the Varicol process. The invention provides enhanced separation of paraxylene using a simulated moving bed process and more flexibility in optimization of a simulated moving bed system with dual rotary valves, and more closely mimics a true Varicol operating scheme, which has been limited to simulated moving bed processes with individual or block valves. This result is achieved by aligning the second rotary valve one bed off of the first rotary valve and switching the flows from one rotary valve to the other during a step time. Additionally, the flows through each valve may be varied during each cycle as in a PowerFeed process.

In one aspect, the process comprises directing the flow of a feed stream and a desorbent stream to, and the flow of at least one raffinate stream and an extract stream away from, a plurality of adsorptive beds with a first rotary valve and a second rotary valve. At the beginning of a first step time interval, the flow of at least one of the feed stream, desorbent stream, at least one raffinate stream, and extract stream is directed to or away from the adsorptive beds by the first rotary valve, and then the flow of at least one of the streams to or away from the adsorptive beds is switched to the second rotary valve after a first subinterval of the first step time interval. The first and second rotary valves comprise a plurality of ports in fluid communication with a plurality of conduits in fluid communication with the plurality of adsorptive beds, with the number of adsorptive beds and ports in each rotary valve being equal (i.e., if there are 8 beds, there are 8 ports in each of the first and second rotary valves, each port connected to the 8 beds by a conduit). The relative spacial position of the ports for the feed stream, desorbent stream, at least one raffinate stream, and extract stream in the first rotary valve is the same as the relative spacial position of the corresponding ports for the feed stream, desorbent stream, at least one raffinate stream, and extract stream in the second rotary valve, and the second rotary valve is positioned so that each stream directed to or from the second rotary valve is one bed away from its corresponding stream directed to or from the first rotary valve.

At the end of the first step time interval, the flows of the feed stream, desorbent stream, at least one raffinate stream, the extract stream are discontinued by the first and second rotary valves. In one embodiment, the first and second rotary valves are then rotated one position downstream, and the flow of at least one of the feed stream, desorbent stream, at least one raffinate stream, and extract stream to or away from the adsorptive beds is resumed by the first rotary valve at the beginning of a second step time interval. After a first subinterval of the second step time interval, the flow of at least one of the feed stream, desorbent stream, at least one raffinate stream, and extract stream to or away from the adsorptive beds is switched from first rotary valve to the second rotary valve, and the process is repeated for a total number of step time intervals equal to the number of adsorptive beds.

In another embodiment, the first rotary valve is rotated two positions downstream at the end of the first step time interval, and the flow of at least one of the feed stream, desorbent stream, at least one raffinate stream, and extract stream to or away from the adsorptive beds is directed by the second rotary valve at the beginning of a second step time interval. After a first subinterval of the second step time interval, the flow of at least one of the feed stream, desorbent stream, at least one raffinate stream, and extract stream to or away from the adsorptive beds is switched from second rotary valve to the first rotary valve. The flows of the feed stream, desorbent stream, at least one raffinate stream, the extract stream are then discontinued by the first and second rotary valves at the end of the second step time interval, and the second rotary valve is rotated two positions downstream. The flows of the feed stream, desorbent stream, at least one raffinate stream, the extract stream are then directed by the first rotary valve and the process repeats for a total number of step time intervals equal to the number of adsorptive beds.

In another aspect, a process for separating paraxylene from a mixture of $C_8$ aromatics in a simulated moving bed adsorptive apparatus is provided, where the simulated moving bed adsorptive apparatus comprises multiple adsorptive beds containing adsorbent material and a first rotary valve and a second rotary valve. At the beginning of a first step time interval, a feed stream, which comprises $C_8$ aromatics, is introduced into the simulated moving bed adsorptive apparatus by the first rotary valve, and a desorbent stream, which comprises desorbent, is introduced into the simulated moving bed adsorptive apparatus by the first rotary valve or second rotary valve. Also at the beginning of the first step time interval, an extract stream, which comprises desorbent and paraxylene, is withdrawn from the simulated moving bed adsorptive apparatus by the first rotary valve, and at least one raffinate stream, which comprises at least one C8 aromatic different from paraxylene, is withdrawn from the simulated moving bed adsorptive apparatus by the first rotary valve or second rotary valve. A flow of circulating fluid is maintained throughout the simulated moving bed adsorptive apparatus. After a first subinterval of the first step time interval, the flow of the feed stream, at least one raffinate stream, or extract stream to or from the adsorptive beds is switched from the first rotary valve to the second rotary valve. At the end of the first step time interval, the flow of the feed stream, desorbent stream, at least one raffinate stream, and extract stream is discontinued by the first and second rotary valves, and the first and second rotary valves are rotated to a bed one position downstream. The process is then repeated for a total number of step time intervals equal to the number of adsorptive beds.

The rate of flow of any of the streams may be varied during a step to implement a PowerFeed operation of the process. For example, the rate of flow of the feed stream may vary during a step time interval, the rate of flow of the desorbent stream may vary during a step time interval, the rate of flow of the raffinate stream may vary during a step time interval, and the rate of flow of the extract stream may vary during a step time interval.

DETAILED DESCRIPTION

Figure 1:
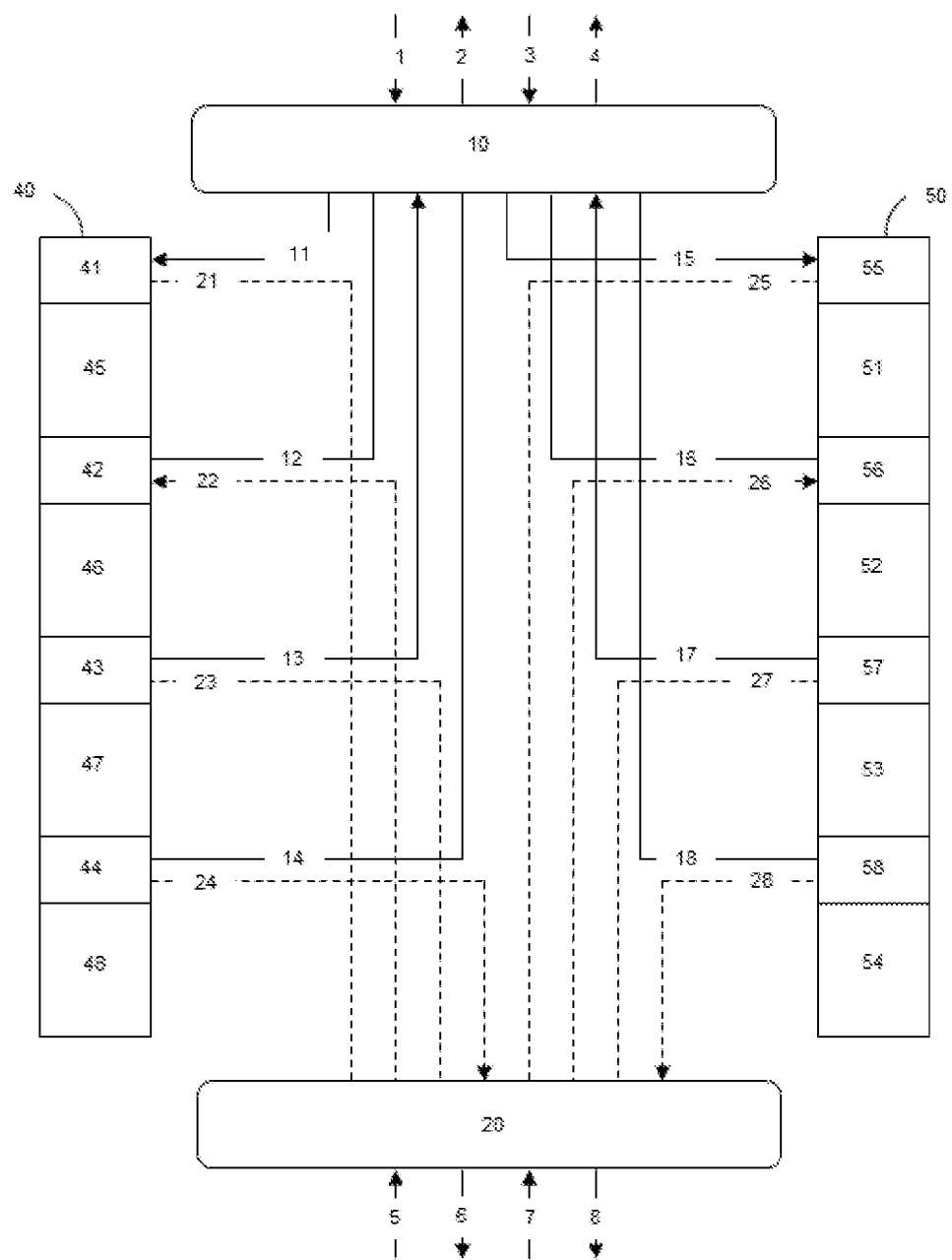
FIG. 1 is a schematic illustration of a simulated moving bed adsorptive separation system with two rotary valves and eight (8) adsorptive beds.

The present invention involves using two rotary valves to provide a Varicol process to enhance the separation of product from a multicomponent feed.

Definitions

Various terms used in this description will be understood in the context of this description. A further explanation of certain terms used herein is provided below.

$C_8$ aromatics are aromatic compounds having 8 carbon atoms. Examples of $C_8$ aromatics include paraxylene, metaxylene, orthoxylene, and ethylbenzene.

Equilibrium xylene is a mixture of $C_8$ aromatics having a thermodynamic equilibrium concentration of the various $C_8$ aromatic compounds when the $C_8$ aromatics are subjected to non-selective isomerization conditions. Equilibrium xylene may be produced in a non-selective process for producing xylenes. A non-selective process for producing xylenes may involve reacting reactants over a non-selective catalyst. Equilibrium xylene may be produced, for example, in a xylene isomerization process, a transalkylation process or a reforming process. Equilibrium xylene may also be produced by other processes. Equilibrium xylene may comprise, for example, about 23 percent paraxylene, based on the total of the xylenes.

Enhanced paraxylene is a mixture of $C_8$ aromatics having a greater concentration of paraxylene than equilibrium xylene. Enhanced paraxylene may be produced in a selective process for producing xylenes. A selective process for producing xylenes may involve reacting reactants over a selective catalyst. Enhanced paraxylene may be produced, for example, by a selective toluene disproportion process or a selective toluene alkylation process. Enhanced paraxylene may also be produced by other processes Enhanced paraxylene may have a concentration of, for example, at least 75% paraxylene, based on the total of $C_8$ aromatics.

A non-selective process for producing xylenes is a process which produces equilibrium xylenes. A non-selective process for producing xylenes may take place over a non-selective catalyst. Examples of non-selective catalysts include large pore zeolites, such as zeolite X and zeolite Y, or amorphous aluminosilicates. When toluene is disproportionated over a large pore size zeolite, equilibrium zeolites may be produced.

A selective process for producing paraxylene (PX) is a process which produces paraxylene in preference to other xylene isomers (MX and OX). A selective process for producing paraxylene may be produced, for example, by a catalytic process over a paraxylene selective catalyst. Examples of paraxylene selective catalysts include medium pore size zeolites, such as ZSM-5, modified with selectivating agents. Selectivating agents may neutralize surface catalytic sites or narrow the pores of the catalyst. Examples of paraxylene selective catalysts and selectivating agents are provided by in U.S. Pat. No. 5,365,004, International Publication No. WO 2013/330093, and U.S. Pat. No. 4,088,706.

Circulating bulk fluid is the fluid (i.e., liquid) which flows in a continuous manner through a simulated moving bed adsorption apparatus. The concentration of compounds in this circulating bulk fluid changes as this fluid flows through the apparatus due to, inter alia, adsorption and desorption of compounds, withdrawal of fluids in extract and reformate streams, and introduction of fluids through feed, desorbent and flush streams.

Unless otherwise specified herein, the terms, downstream and upstream, refer to the direction of flow of circulating bulk fluid.

A number of abbreviations are used herein. PX stands for paraxylene. MX stands for metaxylene. OX stands for orthoxylene. EB stands for ethylbenzene. pDEB stands for paradiethylbenzene. TOL stands for toluene. NA stands for non-aromatics. Non-aromatics, such as paraffins, may be introduced into an adsorption apparatus as a feed impurity, especially when the feed comprises $C_8$ aromatics obtained from a reforming process.

Recovery of Paraxylene from $C_8$ Aromatics Using SMB Separation

The simulated moving bed (SMB) adsorptive separation may take place in an apparatus comprising multiple adsorbent beds containing adsorbent material, e.g., multiple adsorptive beds, stacked one on top of the other. The apparatus comprising multiple adsorptive beds may comprise from 5 to 50, for example, from 5 to 32, for example 8 or 24 adsorbent beds. A circulating bulk fluid may flow in a continuous manner into the top of an adsorbent bed, through the adsorbent bed and down to the top of the next adsorbent bed, and so on. The flow of liquids to and from the adsorbent beds may be controlled by two rotary valves, such that, over time, each stream is introduced into or withdrawn from each of the adsorbent beds of the apparatus. Each rotary valve has multiple ports in fluid communication with multiple conduits in fluid communication with the multiple adsorptive beds, with the number of adsorptive beds and ports in each rotary valve being equal. In other words, if the apparatus has 8 adsorptive beds, each rotary valve has 8 ports, each port connected to an adsorptive bed by a conduit. The relative spacial position of the ports for the feed stream, desorbent stream, at least one raffinate stream, and extract stream in the first rotary valve is the same as the relative spacial position of the corresponding ports for the feed stream, desorbent stream, at least one raffinate stream, and extract stream in the second rotary valve.

The multicomponent feed may comprise a $C_8$ aromatic mixture of paraxylene, orthoxylene, metaxylene, and ethylbenzene. This $C_8$ aromatic mixture may comprise equilibrium xylenes with a concentration of paraxylene from 15 to 30 volume percent, for example, from 15 to 27 volume percent, for example, from 21 to 24 volume percent. The multicomponent feed of step (a) may also comprise enhanced paraxylene having a concentration of from 70 to 85 volume percent, for example, from 70 to 80 volume percent, paraxylene.

When ethylbenzene is separated from metaxylene and/or orthoxylene, the feed may comprise at least 5 weight percent ethylbenzene, less than 2 weight percent paraxylene, and at least 50 weight percent of the sum of metaxylene and orthoxylene.

According to one embodiment, at least 50 volume percent of the $C_8$ aromatic mixture may be produced by at least one refinery or petrochemical process. Examples of refinery or petrochemical processes for producing equilibrium xylenes include a reforming process, an isomerization process, a transalkylation process, and a mixture of any of these processes. An example of a refinery or petrochemical process for producing enhanced paraxylene, which comprises from 75 to 98 volume percent of paraxylene, is a selective toluene disproportionation process, a selective benzene or toluene methylation process, or a selective process for converting methanol to paraxylene.

When paraxylene is separated from a mixture of $C_8$ aromatics, the desorbent, which is introduced into the simulated moving bed adsorption apparatus via the desorbent stream, may comprise, for example, paradiethylbenzene, toluene or tetralin. A tetralin desorbent is described in U.S. Pat. No. 8,283,274.

When paraxylene is separated from a mixture of $C_8$ aromatics, the extract stream may comprise at least 99.7 volume percent of paraxylene, based on the total volume of xylenes and ethylbenzene present in the extract stream. The extract stream may be separated by distillation downstream to provide a purified paraxylene product and a stream rich in desorbent, which may be recycled for re-use in the simulated moving bed adsorptive process.

One or more raffinate streams may be withdrawn from the simulated moving bed adsorptive apparatus. When a single raffinate stream is withdrawn from a simulated moving bed adsorption apparatus for separating paraxylene, the raffinate stream may comprise desorbent, metaxylene, orthoxylene, and ethylbenzene. This raffinate stream is withdrawn from a bed of the simulated moving bed adsorptive separation unit through a conduit and then through a liquid distribution device, such as a rotary valve. The bed, from which the raffinate stream is withdrawn, is downstream, based on the direction of the flow of circulating bulk fluid, from the bed into which feed is introduced.

The raffinate stream may be distilled to obtain a stream enriched in desorbent and a stream enriched in $C_8$ aromatics, such as metaxylene, orthoxylene, and ethylbenzene. The desorbent may be recycled for re-use in the simulated moving bed adsorptive process. The $C_8$ aromatics from the distillation may be isomerized in the liquid phase, vapor phase, or a combination thereof. In particular, these $C_8$ aromatics may be passed to an isomerization unit to obtain an isomerized product stream comprising from 15 to 30 volume percent, for example, from 20 to 30 volume percent of paraxylene. The isomerized product stream may then be recycled to the simulated moving bed adsorptive apparatus.

FIG. 1

FIG. 1 is a schematic illustration of a simulated moving bed apparatus with two rotary valves (i.e., rotary valves 10 and 20). This simulated bed apparatus further includes eight adsorbent beds (i.e., adsorbent beds 45, 46, 47, 48, 51, 52, 53, and 54). For the purposes of FIG. 1, adsorbent bed 45 is also referred to herein as the first adsorbent bed, adsorbent bed 46 is also referred to herein as the second adsorbent bed, adsorbent bed 47 is also referred to herein as the third adsorbent bed, adsorbent bed 48 is also referred to herein as the fourth adsorbent bed, adsorbent bed 51 is also referred to herein as the fifth adsorbent bed, adsorbent bed 52 is also referred to herein as the sixth adsorbent bed, adsorbent bed 53 is also referred to herein as the seventh adsorbent bed, and adsorbent bed 54 is also referred to herein as the eighth adsorbent bed.

The adsorbent beds are separated from one another by fluid collection areas 41, 42, 43, 44, 55, 56, 57, and 58. Additional fluid collection areas (not shown in FIG. 1) may also be positioned at the bottom of columns 40 and 50 below beds 48 and 54. These fluid collection areas correspond to downcomers as described in U.S. Pat. No. 3,201,491. The adsorbent beds include adsorbent material, whereas the collection areas are free of adsorbent material.

In FIG. 1, adsorbent beds are stacked in two columns 40 and 50. However, it will be understood that other configurations are possible. For example, the adsorbent beds may stand alone, unstacked or may be stacked in one column or in more than two columns.

In operation, a circulating bulk fluid flows through each of the adsorbent beds and collection areas. Circulating bulk fluid enters collection area 41 through a conduit not shown in FIG. 1. This fluid flows downward through a first column 40 of adsorbent beds through, in sequence, area 41, bed 45, area 42, bed 46, area 43, bed 47, area 44, and bed 48. Fluid passing from the bottom of bed 48 is passed (through a conduit not shown in FIG. 1) to fluid collection area 55. This fluid then flows downward through a second column 50 of adsorbent beds through, in sequence, area 55, bed 51, area 56, bed 52, area 57, bed 53, area 58, and bed 54. To complete the loop of circulating bulk fluid, fluid is passed from the bottom of bed 54 (through a conduit not shown in FIG. 1) to fluid collection area 41.

Each rotary valve includes two input streams and two withdrawal streams. A feed stream 1 and a desorbent stream 3 are introduced as input streams into rotary valve 10. Similarly, a feed stream 5 and a desorbent stream 7 are introduced as input streams into rotary valve 20. Also, an extract stream 2 and a raffinate stream 4 are withdrawn as withdrawal streams from rotary valve 10. Similarly, an extract stream 6 and a raffinate stream 8 are withdrawn from rotary valve 20.

The feed stream 1 and the desorbent stream 3 are directed by rotary valve 10 to the collection areas 41, 42, 43, 44, 55, 56, 57, and 58, via conduits 11, 12, 13, 14, 15, 16, 17, and 18. Similarly, an extract stream and a raffinate stream are withdrawn from the collection areas 41, 42, 43, 44, 55, 56, 57, and 58, and passed to rotary valve 10, via conduits 11, 12, 13, 14, 15, 16, 17, and 18. Rotary valve 10 diverts these withdrawn streams to extract withdrawal stream 2 and raffinate withdraw stream 4. Also, the feed stream 5 and the desorbent stream 7 are directed by rotary valve 20 to the collection areas 41, 42, 43, 44, 55, 56, 57, and 58, via conduits 21, 22, 23, 24, 25, 26, 27, and 28. Similarly, an extract stream and a raffinate stream may be taken from the collection areas 41, 42, 43, 44, 55, 56, 57 and 58, and passed to rotary valve 20, via conduits 21, 22, 23, 24, 25, 26, 27, and 28. Rotary valve 20 diverts these streams to extract withdrawal stream 6 and raffinate withdraw stream 8.

In operation, each rotary valve is capable of directing streams to and from varying positions of the adsorbent beds. Arrows in conduits 11, 13, 15, and 17 represent the direction of flow of streams during a first step. The first step (i.e., step 1) lasts for a fixed time interval. At the beginning of the first step time interval, rotary valve 10 directs the flow of a feed stream from conduit 1 through conduit 11 to collection area 41. The feed is carried along with the circulating bulk fluid and flows downward into the first adsorbent bed 45. At the beginning of the first step time interval, rotary valve 10 also directs the flow of a desorbent stream from conduit 3 through conduit 15 to collection area 55, the flow of a raffinate stream from collection area 43 through conduit 13 to raffinate withdraw stream 4, and the flow of an extract stream from collection area 57 through conduit 17 to extract withdraw stream 2.

During the first step time interval, after a first subinterval, the flow in at least one of conduits 11, 13, 15, and 17 is interrupted and flow through at least one of conduits 22, 24, 26, and 28 is started. Arrows in conduits 11, 13, 15, and 17 represent the direction of potential flows to and from rotary valve 10 during the first step time interval. It will be appreciated that rotary valve 20 is configured to direct flows one bed downstream from the corresponding stream directed by rotary valve 10. In particular, during the first step time interval, rotary valve 10 is configured to direct flow of feed to first bed 45, via conduit 11 and collection area 41, whereas rotary valve 20 is configured to direct flow of feed to second bed 46, via conduit 22 and collection area 42. Similarly, during the first step time interval, rotary valve 10 is configured to direct flow of desorbent to fifth bed 51, via conduit 15 and collection area 55, whereas rotary valve 20 is configured to direct flow of desorbent to sixth bed 52, via conduit 26 and collection area 56. Also, during the first step time interval, rotary valve 10 is configured to direct flow of raffinate from second bed 46, via conduit 13 and collection area 43, whereas rotary valve 20 is configured to direct flow of raffinate from third bed 47, via conduit 24 and collection area 44. Also, during the first step time interval, rotary valve 10 is configured to direct flow of extract from sixth bed 52, via conduit 17 and collection area 57, whereas rotary valve 20 is configured to direct flow of extract from seventh bed 53 via conduit 28 and collection area 58.

At the end of the first step time interval, the flow of streams to and from rotary valves 10 and 20 is discontinued. Before the second step (i.e., step 2) begins, either (a) both rotary valves 10 and 20 are shifted one position, such that the flow of streams to and from the rotary valves are moved one collection area downstream from the position of step 1, or (b) rotary valve 10 is shifted two positions downstream, whereas rotary valve 20 remains in the same position as step 1.

Referring to FIG. 1, according to the first embodiment where both rotary valves shift flow patterns, before step 2 begins, rotary valves 10 shifts to reconfigure the flow of feed, raffinate, desorbent, and extract streams. In particular, the direction of flow of feed is shifted from conduit 11 to conduit 12, such that feed can flow into collection area 42. Also, the direction of flow of raffinate is shifted from collection area 43 to collection area 44, such that raffinate can flow through conduit 14. Also, the direction of flow of desorbent is shifted from conduit 15 to conduit 16, such that desorbent is redirected into collection area 56. Also, the direction of flow of extract is shifted from collection area 57 to collection area 58, such that extract can flow through conduit 18.

According to the first embodiment where both rotary valves shift flow patterns, before step 2 begins, rotary valve 20 shifts in a manner which reflects the shift of rotary valve 10. In particular, the direction of flow of feed is shifted from conduit 22 to conduit 23, such that feed is can flow into collection area 43. Also, the direction of flow of raffinate is shifted from collection area 44 to collection area 55, such that raffinate can flow through conduit 25. Also, the direction of flow of desorbent is shifted from conduit 26 to conduit 27, such that desorbent is redirected into collection area 57. Also, the direction of flow of extract is shifted from collection area 58 to collection area 41, such that extract can flow through conduit 21.

In this first embodiment, step 2 is conducted in the same manner as step 1. In particular, at the beginning of the second step time interval, the flow of all four of the streams (i.e., feed, raffinate, desorbent, and extract streams) is directed from rotary valve 10. Also during step 2, the flow of at least one stream is shifted one bed downstream by discontinuing the flow of the stream from rotary valve 10 and resuming the flow of the stream from rotary valve 20 after a subinterval of the step time interval. The process involves a total number of step time intervals equal to the number of beds. Thus, in this embodiment, there are 8 step time intervals. Steps 3-8 are conducted in the same manner as steps 1 and 2, with rotary valves 10 and 20 being shifted in the same manner between steps. After all eight steps are completed, a first cycle of steps is completed, and the cycle is repeated.

In the second embodiment, before step 2 starts, rotary valve 10 is shifted two positions and rotary valve 20 remains fixed. In particular, the direction of flow of feed from rotary valve 10 is shifted from conduit 11 to conduit 13, such that feed is can flow into collection area 43. Also, the direction of flow of raffinate is shifted from collection area 43 to collection area 55, such that raffinate can flow through conduit 15. Also, the direction of flow of desorbent is shifted from conduit 15 to conduit 17, such that desorbent is redirected into collection area 57. Also, the direction of flow of extract is shifted from collection area 57 to collection area 41, such that extract can flow through conduit 11.

In the second embodiment, the direction of flow of streams to and from rotary valve 20, remains fixed before step two begins. Rotary valve 20 remains configured to direct the flow of feed through conduit 21, the flow of raffinate through conduit 24, the flow of desorbent through conduit 26 and the flow of extract through conduit 28.

In the second embodiment, at the beginning of the second step time interval, the flow of streams is initially directed by rotary valve 20. Also during step 2, the flow of at least one stream shifted one bed downstream by discontinuing the flow of the stream from rotary valve 20 and resuming the flow of the stream from rotary valve 10. Steps 3 and 4, steps 5 and 6, and steps 7 and 8 are conducted in the same manner as steps 1 and 2, with the upstream rotary valve being shifted two beds downstream between steps. After all eight steps are completed, a first cycle of steps is completed, and the cycle is repeated.

Each step of the eight step cycle may take place for a set time interval. Each shift of flow control of streams from one rotary valve to another may take place within a set time subinterval. For example, in step 1, the flow of the extract stream may be switched from rotary valve 10 to rotary valve 20 after a first time subinterval. Then, the flow of the raffinate stream may be switched from rotary valve 10 to rotary valve 20 after a second time subinterval. Then, the flow of the feed stream may be switched from rotary valve 10 to rotary valve 20 after a third time subinterval. The time subintervals for switching between valves may be the same for each step of the eight step cycle.

FIG. 2

Figure 2:
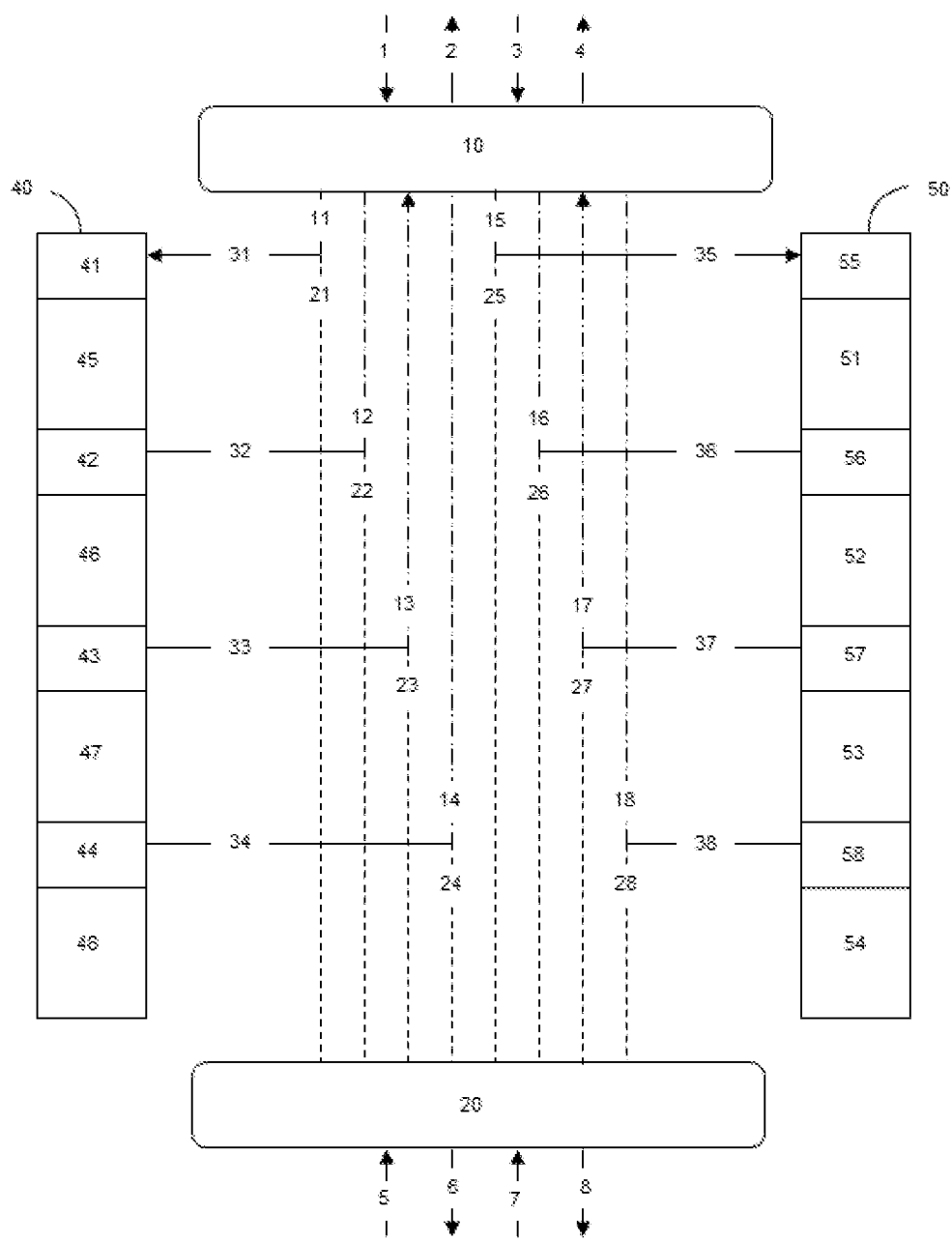
FIG. 2 is a schematic illustration of a modification of the simulated moving bed adsorptive separation shown in FIG. 1.

FIG. 2 illustrates an embodiment where streams flow to and from collection areas 41-44 and 55-58 through a common conduit in fluid connection with both rotary valves 10 and 20.

FIG. 1 is a schematic diagram. FIG. 1 does not represent any particular type of apparatus of directing flow of streams to and from columns 40 and 50 and rotary valves 10 and 20. The flow of streams between these streams may be directed through a variety of patterns and equipment. FIG. 2 illustrates one example of a way of transporting streams to and from columns 10 and 20.

In FIG. 2, all of the elements of columns 40 and 50, rotary valves 10 and 20, and conduits 1-8 are the same as FIG. 1. Conduits 11-18, which extend from and return to rotary valve 10, and conduits 21-28 which extend from and return to rotary valve 20 in FIG. 1 correspond to the same numbered conduit in FIG. 2.

In FIG. 1, conduits extending from and returning to rotary valves 10 and 20 are identified by solid lines and dashed lines. In particular, conduits 11-18, which are in fluid communication between rotary valve 10 and columns 40 and 50, are depicted in FIG. 1 as solid lines. Also, conduits 21-28 in fluid communication between rotary valve 20 and columns 40 and 50 are depicted as dashed lines, having the following even pattern:

In FIG. 2, conduits 21-28 extending from rotary valve 20 are also depicted as dashed lines, having the following even pattern:

In FIG. 2, conduits 11-18 extending from rotary valve 10 are also depicted as dashed lines, having the following uneven pattern:

Conduits 11-18 and conduits 21-28 in FIG. 2 intersect at conduits 31-38. Conduits 31-38 represent a common conduit for transporting fluid to and from collection areas 41-58 to and from rotary valves 10 and 20. For example, during a first step time interval of step 1, the flow of feed from rotary valve 10 may first be introduced into collection area 41 through conduits 11 and 31. After a subinterval of the first step time interval, the flow of feed from rotary valve 10 though conduits 11 and 31 may be interrupted and the flow of feed from rotary valve 20 may be started through conduits 22 and 32 to collection area 42.

It will be understood that FIG. 2 represents only one option for routing fluids to and from rotary valves 10 and 20 to and from columns 40 and 50. Another option would be to eliminate shared conduits 31-38 and to have individual conduits in fluid communication between rotary valve 10 and columns 40 and 50, and to have individual conduits in fluid communication between rotary valve 20 and columns 40 and 50.

FIG. 3

Figure 3:
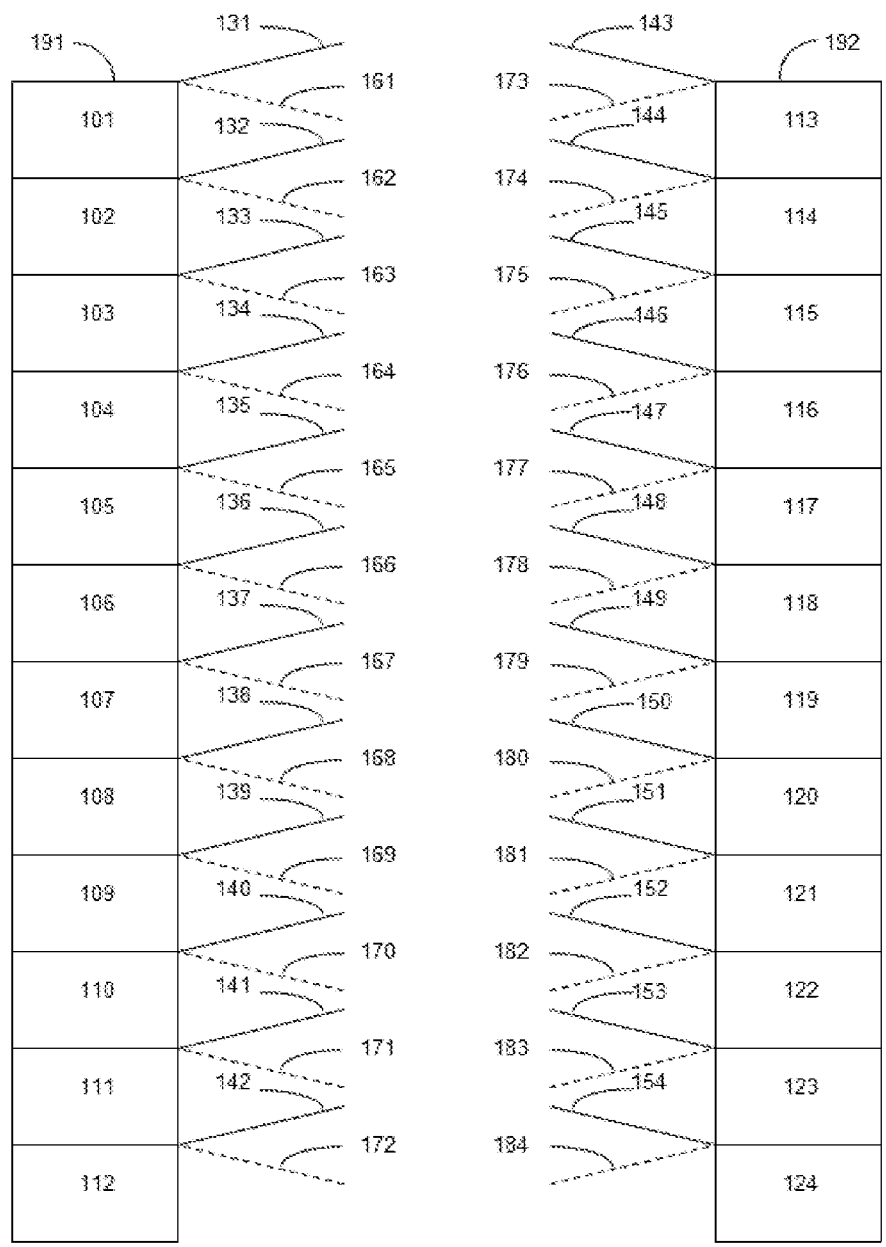
FIG. 3 is a schematic illustration of a simulated moving bed adsorptive separation with two rotary valves and twenty four (24) adsorptive beds.

FIG. 3 illustrates a simulated moving bed apparatus with 24 adsorbent beds. This 24 bed configuration is particularly useful for separating one $C_8$ aromatic, such as paraxylene, from a mixture of $C_8$ aromatics, such as a mixture of paraxylene, metaxylene, orthoxylene and ethylbenzene.

In FIG. 3, twelve adsorbent beds 101-112 are stacked in a first column 191 and another twelve adsorbent beds 113-124 are stacked in a second column 192. Conduits in fluid communication with a first rotary valve are depicted by solid lines 131-154, and conduits in fluid communication with a second rotary valve are depicted by dashed lines 161-184. For simplicity, the first and second rotary valves are not shown in FIG. 3. However, it will be understood that the first rotary valve would correspond to rotary valve 10 in FIGS. 1 and 2, and that the second rotary valve would correspond to rotary valve 20 in FIGS. 1 and 2. The first and second rotary valves, not shown in FIG. 3, would include 24 ports each for accommodating the extra conduits shown in FIG. 3. Also, not shown in FIG. 3 are collection areas between beds. However, it will be understood that such collection areas, such as those represented by collection areas 41-44 and 55-58 in FIGS. 1 and 2, may be present in columns 191 and 192 of FIG. 3.

At the beginning of an adsorption cycle, a feed, such as a mixture of paraxylene, metaxylene, orthoxylene, and ethylbenzene, may be introduced into the top of column 191 and the first bed 101, via conduit 131 and the first rotary valve. A circulating bulk fluid, which is taken from the bottom of column 192 and bed 124, may also be introduced into the top of column 191 and bed 101 through a conduit not shown in FIG. 3. The circulating bulk fluid flows in a downward direction through each of the beds of the first column 191 and is then transported to the top of the second column 192, through a conduit not shown in FIG. 3. The circulating bulk fluid then flows in a downward direction through each of the beds of the second column 192.

At the same time that the flow of feed is started, a raffinate stream may be withdrawn from the top of a bed downstream from the first bed 101. For example, this raffinate stream may be taken from the top of the tenth bed 110 via conduit 140 and the first rotary valve. When the feed is a mixture of paraxylene, metaxylene, orthoxylene, and ethylbenzene, the raffinate stream would comprise a desorbent, metaxylene, orthoxylene, and ethylbenzene.

At the same time that the flow of feed is started, a desorbent stream may be introduced into the top of a bed downstream from the ninth bed 109. For example, this desorbent stream may be introduced into the top of the twelfth bed 112 via conduit 142 and the first rotary valve. When the feed is a mixture of paraxylene, metaxylene, orthoxylene, and ethylbenzene, the desorbent may be, for example, paradiethylbenzene or toluene.

At the same time that the flow of feed is started, an extract stream may be withdrawn from the top of a bed downstream from the twelfth bed 112 and upstream from the first bed 101. For example, this extract stream may be taken from the top of the seventeenth bed 117 via conduit 147 and the first rotary valve. When the feed is a mixture of paraxylene, metaxylene, orthoxylene, and ethylbenzene, the raffinate stream would comprise a desorbent, metaxylene, orthoxylene, and ethylbenzene.

At the same time that the first rotary valve is positioned to direct the flow of the feed stream to the top of the first bed 101, the flow of the raffinate stream from the top of the tenth bed 110, the flow of the desorbent stream to the top of the twelfth bed 112, and the flow of the extract stream from the top of the seventeenth bed 117, the second rotary valve would be positioned to direct the flow of the corresponding stream one bed downstream from these streams. In particular, the second rotary valve would be positioned to direct the flow of the feed stream to the top of the second bed 102 via conduit 162, the second rotary valve would be positioned to direct the flow of the raffinate stream from the top of the eleventh bed 111 via conduit 171, the second rotary valve would be positioned to direct the flow of the desorbent stream to the top of the thirteenth bed 113 via conduit 173, and the second rotary valve would be positioned to direct the flow of the extract stream from the top of the eighteenth bed 118 via conduit 178.

At the start of a first step time interval of the cycle, the first rotary valve directs the flow of all of the streams to and from beds in columns 191 and 192. However, after the expiration of at least one subinterval of the first step time interval, the flow of at least one stream is discontinued to or from the first rotary valve and is started to or from the second rotary valve. For example, after a first subinterval, the flow of the extract stream from the top of bed 117 via the first rotary valve and conduit 147 may be discontinued and simultaneously started from bed 117 via the second rotary valve and conduit 178. After a second subinterval, the flow of the raffinate stream from the top of bed 110 via the first rotary valve and conduit 140 may be discontinued and simultaneously started from bed 110 via the second rotary valve and conduit 171. After a third subinterval, the flow of the feed stream to the top of bed 101 via the first rotary valve and conduit 131 may be discontinued and simultaneously started to bed 102 via the second rotary valve and conduit 162.

At the end of the first step time interval, the flow of streams to and from both rotary valves is discontinued, and each rotary is shifted one position to direct flows to beds one bed downstream from step 1. The flow of streams as done during step 1 is repeated. After a total number of step time intervals equal to the number of beds, 24 in this embodiment, a first cycle of steps is completed, and the cycle is repeated.

During operation, the beds of the simulated moving bed apparatus shown in FIG. 3 may be considered to be divided into four zones. These zones are (1) the adsorption zone, (2) the purification zone, (3) the desorption zone, and (4) the buffer zones. The purification zone has also been referred to being the rectification zone. These zones are described in the art, for example, in U.S. Pat. No. 8,569,564.

At the start of the first step time interval, as described above, the adsorption zone extends from the top of the first bed 101 to the bottom of the ninth bed 109, the purification zone extends from the bottom of the sixteenth bed 116 to the bottom of the twenty-fourth bed 124, the desorption zone extends from the top of the twelfth bed 112 to the bottom of the sixteenth bed 116, and the buffer zone extends from the bottom of the ninth bed 109 to the top of the twelfth bed 112. Thus, at the start of the first step time interval, the adsorption zone has nine (9) beds 101-109, the purification zone has eight (8) beds 117-124, the desorption zone has five (5) beds 112-116, and the buffer zone has two (2) beds 110-111.

After the first subinterval of the first step time interval described above, where control of the flow of the extract stream is switched from the first rotary valve to the second valve, the desorption zone is expanded by one bed, and the purification zone is contracted by one bed. In particular, the desorption zone is expanded to include six (6) beds 112-117, and the purification zone is contracted to include seven (7) beds 118-124.

After the second subinterval of the first step time interval described above, where control of the flow of the raffinate stream is switched from the first rotary valve to the second valve, the adsorption zone is expanded by one bed, and the buffer zone is contracted by one bed. In particular, the adsorption zone is expanded to include ten (10) beds 101-110, and the buffer zone is contracted to include one (1) bed 111.

After the third subinterval of the first step time interval described above, where control of the flow of the feed stream is switched from the first rotary valve to the second valve, the purification zone is expanded by one bed, and the adsorption zone is contracted by one bed. In particular, the purification zone is expanded to include seven (7) beds 118-124 and 101, and the adsorption zone is contracted to include nine (9) beds 102-110.

After the first step time interval and at the start of the second step time interval, each of the zones is shifted one bed downstream from the beginning of the first step. In particular, at the start of the second step, the adsorption zone has nine (9) beds 102-110, the purification zone has eight (8) beds 118-124 and 101, the desorption zone has five (5) beds 113-117, and the buffer zone has two (2) beds 111-112. As step 2 proceeds, zones expand and contract in the same manner as the first step.

FIG. 4

Figure 4:
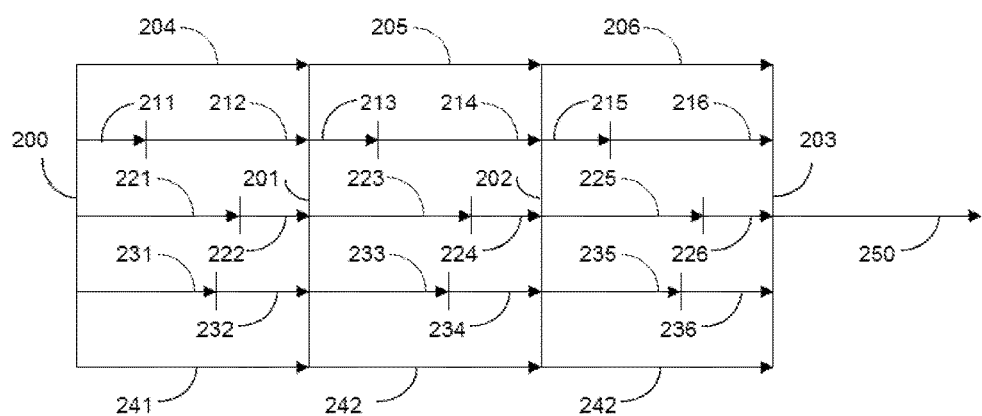
FIG. 4 is a series of timelines showing flows of streams during multiple step time intervals.

FIG. 4 provides a parallel series of five timelines to depict the timing of events during a series of steps of a simulated moving bed process.

Vertical line 200 represents the beginning of the first step time interval, vertical line 201 represents the end of the first step time interval and the beginning of the second step time interval, vertical line 202 represents the end of the second step time interval and the beginning of the third step time interval, and horizontal line 203 represents the end of the third step time interval and the beginning of the fourth step time interval.

The three horizontal arrows 204-206 at the top of FIG. 4 represent the duration of each of the first three steps of a simulated moving bed process. Each step lasts for a fixed time interval.

The six horizontal arrows 211-216 represent the flow of an extract stream during the first three steps. The flow of the extract stream changes from one rotary valve to the other during each step after a fixed time subinterval. This fixed time subinterval is represented by arrows 211, 213, and 215.

The six horizontal arrows 221-226 represent the flow of a feed stream during the first three steps. The flow of the feed stream changes from one rotary valve to the other during each step after a fixed time subinterval. This fixed time subinterval is represented by arrows 221, 223, and 225.

The six horizontal arrows 231-236 represent the flow of a raffinate stream during the first three steps. The flow of the raffinate stream changes from one rotary valve to the other during each step after a fixed time subinterval. This fixed time subinterval is represented by arrows 231, 233, and 235.

The three horizontal arrows 241-243 represent the flow of a desorbent stream during the first three steps. The flow of the desorbent stream does not change during each step.

Arrow 250 represents the remaining steps of a cycle. In embodiments with 8 adsorbent beds as shown in FIGS. 1 and 2, there are five (5) remaining steps in the cycle. In embodiments with 24 adsorbent beds as shown in FIG. 3, there are twenty-one (21) remaining steps in the cycle.

Referring to FIG. 4 in connection with FIG. 3, in an example of an embodiment described above, at the beginning of the first step time interval, as represented by horizontal line 200 of FIG. 4, the flow of streams into and out of beds in columns 191 and 192 of FIG. 4 is controlled by a first rotary valve. For example, the first rotary valve directs (a) the flow of the feed stream to the top of bed 101 via conduit 131, (b) the flow of the raffinate stream from the top of bed 110 via conduit 140, (c) the flow of the desorbent stream to the top of bed 112 via conduit 142, and (d) the flow of the extract stream from the top of bed 117 via conduit 147.

After a first time subinterval, represented in FIG. 4 by arrow 211, control of the flow of the extract stream is switched from the first rotary valve to the second rotary valve. Consequently, the extract stream flows from the top of bed 118 through conduit 178 for the remainder of the first step time interval, as represented by arrow 212.

After a second time subinterval, represented in FIG. 4 by arrow 231, control of the flow of the raffinate stream is switched from the first rotary valve to the second rotary valve. Consequently, the raffinate stream flows from the top of bed 111 through conduit 171 for the remainder of the first step time interval, as represented by arrow 232.

After a third time subinterval, represented in FIG. 4 by arrow 221, control of the flow of the feed stream is switched from the first rotary valve to the second rotary valve. Consequently, the feed stream flows to the top of bed 102 through conduit 162 for the remainder of the first step time interval, as represented by arrow 222.

At the end of the first step time interval, as represented by horizontal line 201 of FIG. 4, the first and second rotary valves are advanced one position, and control of the flow of all four of the streams is returned to the first rotary valve. Consequently, at the start of the second step time interval, the first rotary valve directs (a) the flow of the feed stream to the top of bed 102 via conduit 132, (b) the flow of the raffinate stream from the top of bed 111 via conduit 141, (c) the flow of the desorbent stream to the top of bed 113 via conduit 143, and (d) the flow of the extract stream from the top of bed 118 via conduit 148. The control of flow of streams switching from the first rotary valve to the second rotary valve at the same time subintervals as used in the first step time interval is repeated for the second step time interval, and the remainder of the step time intervals necessary to complete a cycle. Time subintervals 213 and 215 are the same as time subinterval 211, time subintervals 233 and 235 are the same as time subinterval 231, and time subintervals 223 and 225 are the same as time subinterval 221.

In the Examples which follow, results are calculated using mathematical models.

Example 1

This Example describes the use of a dual rotary valve operation of a simulated moving bed process for separating paraxylene from an equilibrium mixture of paraxylene, metaxylene, orthoxylene, and ethylbenzene. The separation takes place in a bed simulated moving bed apparatus as illustrated in FIG. 3.

The first rotary valve (Rotary Valve-1) is configured to direct streams one bed upstream from the configuration of the second rotary valve (Rotary Valve-2).

The feed to the simulated moving bed is composed of 23.6% paraxylene, 49.7% metaxylene, 12.7% orthoxylene and 14.0% ethylbenzene. Conditions are maintained to obtain paraxylene purity at 99.7% and paraxylene recovery at 97.0%. Each step time interval of the simulated moving bed process last for 2.23 minutes (min.). There are four step subintervals in Example 1. During each step of the simulated moving bed process, feed is introduced at a rate of 2.43 m$^3$/min., desorbent is introduced at a rate of 2.43 m$^3$/min., extract is withdrawn at a rate of 1.61 m$^3$/min., and raffinate is withdrawn at a rate of 3.26 m$^3$/min.

At the start of a first step time interval, all liquid flows through a first rotary valve (Rotary Valve-1). In particular, the feed stream flows through Rotary Valve-1 through conduit 144 to the top of bed 114 of FIG. 3. The raffinate stream, which comprises a mixture of metaxylene, orthoxylene, ethylbenzene, and desorbent, is withdrawn from the top of bed 123 via conduit 153 and through Rotary Valve-1. The desorbent stream, which is composed of paradiethylbenzene, flows through Rotary Valve-1 through conduit 131 to the top of bed 101 of FIG. 3. Further, the extract stream, which comprises a mixture of paraxylene and desorbent, is withdrawn from the top of bed 106 via conduit 136 and through Rotary Valve-1.

At the start of the first step time interval, there are five (5) beds (i.e., beds 101-105) in the desorption zone, eight (8) beds (i.e., beds 106-113) in the purification zone, nine (9) beds (i.e., beds 114-122) in the adsorption zone, and two (2) beds (i.e., beds 123 and 124) in the buffer zone. This zone configuration is referred to in this Example as 5:8:9:2.

This initial zone configuration is maintained for a first subinterval of 0.74 min. of the first step. Then, the extract position is switched one column downstream (i.e., from the top of bed 106 to the top of bed 107) by taking extract through Rotary Valve-2 via conduit 167. At this point, the zone configuration becomes 6:7:9:2.

After a second subinterval, which ends at 1.48 min. of the first step time interval, the raffinate port is switched from Rotary Valve-1 to Rotary Valve-2, causing raffinate to flow from the top of bed 124 (instead of the top of bed 123) via conduit 184. This switch results in a new zone configuration of 6:7:10:1.

After a third subinterval, which ends at 1.75 min of the first step, the feed port switched from Rotary Valve-1 to Rotary Valve-2, causing feed to flow into the top of bed 115 (instead of the top of bed 114) via conduit 175. This switch results in a new zone configuration of 6:8:9:1.

After a complete step time interval of 2.23 min, the first step is completed. It is noted that, in Example 1, the position of desorbent stream remains constant during the entire step time interval. At the end of the first step time interval, Rotary Valve-1 and Rotary Valve-2 are shifted one position to direct streams to one bed downstream from the positions at the start of the first step, and a second step is started by flowing streams through Rotary Valve-1. At the start of the second step, there are five (5) beds (i.e., beds 102-106) in the desorption zone, eight (8) beds (i.e., beds 107-114) in the purification zone, nine (9) beds (i.e., beds 115-123) in the adsorption zone, and two (2) beds (i.e., beds 124 and 101) in the buffer zone. The zone configurations at the beginning of the first step and the second step are both 5:8:9:2.

The first step is repeated 23 times to complete a cycle of 24 steps, and then the cycle is repeated.

The process of Example 1 results in a paraxylene productivity of 31.77 ton/hr and a total throughput of 138.38 ton/hr, based on the total amount of feed that is fed to the system.

Example 2 (Comparative)

This Example uses a standard single rotary valve operation of a 24-bed system like that shown in FIG. 3, without Rotary Valve-2 and conduits 161-184. The flow of streams is controlled by a single rotary valve, and the flow of stream remained constant throughout.

The composition of the feed is the same as Example 1. As with Example 1, conditions are maintained to obtain paraxylene purity at 99.7% and paraxylene recovery at 97.0%. The step time interval of Example 2 is slightly longer than the step time interval of Example 1. In particular, each step time interval of Example 2 is 2.29 min., whereas the step time interval of Example 1 is 2.23 min. There are no step subintervals in Example 2.

The flow rates of streams in Example 2 are slightly different than the flow rates of streams in Example 1. In Example 2, feed is introduced at a rate of 2.38 m$^3$/min. (vs. 2.43 m$^3$/min. in Example 1), desorbent is introduced at a rate of 2.30 m$^3$/min. (vs. 2.43 m$^3$/min. in Example 1), extract is withdrawn at a rate of 1.53 m$^3$/min (vs. 1.61 m$^3$/min. in Example 1), and raffinate is withdrawn at a rate of 3.14 m$^3$/min (vs. 3.26 m$^3$/min in Example 1).

At the start of a first step, the feed stream flows through the rotary valve through conduit 144 to the top of bed 114 of FIG. 3. The raffinate stream, which comprises a mixture of metaxylene, orthoxylene, ethylbenzene, and desorbent, is withdrawn from the top of bed 123 via conduit 153. The desorbent stream, which is composed of paradiethylbenzene, flows through conduit 131 to the top of bed 101 of FIG. 3. The extract stream, which comprises a mixture of paraxylene and desorbent, is withdrawn from the top of bed 107 via conduit 137.

At the start of the first step, there are six (6) beds (i.e., beds 101-106) in the desorption zone, seven (7) beds (i.e., beds 107-113) in the purification zone, nine (9) beds (i.e., beds 114-122) in the adsorption zone, and two (2) beds (i.e., beds 123 and 124) in the buffer zone. The zone configuration in Example 2 is 6:7:9:2.

After a complete step time interval of 2.23 min., the first step is completed. The rotary valve is shifted one position to direct streams to one bed downstream from the positions at the start of the first step, and a second step is started by flowing streams through the rotary valve.

The first step is repeated 23 times to complete a cycle of 24 steps, and then the cycle is repeated.

The process of Example 2 results in a paraxylene productivity of 31.09 ton/hr and a total throughput of 135.39 ton/hr, based on the total amount of feed that is fed to the system.

Example 3

Example 3 uses the same dual rotary valve operation as described in Example 1 and shown in FIG. 3, but increases the desorbent to feed ratio to increase the throughput of the process. In Example 1, the desorbent to feed ratio is 1, whereas in Example 3, the desorbent to feed ratio is 2.23.

The composition of the feed is the same as Example 1. As with Example 1, conditions are maintained to obtain paraxylene purity at 99.7% and paraxylene recovery at 97.0%. Each step time interval in Example 3 lasts for 1.91 min There are three step subintervals in Example 3.

In Example 3, feed is introduced at a rate of 2.76 m$^3$/min. (vs. 2.43 m$^3$/min. in Example 1), desorbent is introduced at a rate of 6.16 m$^3$/min. (vs. 2.43 m$^3$/min in Example 1), extract is withdrawn at a rate of 4.55 m$^3$/min. (vs. 1.61 m$^3$/min in Example 1), and raffinate is withdrawn at a rate of 4.37 m$^3$/min. (vs. 3.26 m$^3$/min in Example 1).

At the start of a first step time interval, the feed stream flows through Rotary Valve-1 through conduit 144 to the top of bed 114 of FIG. 3. A raffinate stream, which comprises a mixture of metaxylene, orthoxylene, ethylbenzene, and desorbent, is withdrawn from the top of bed 123 via conduit 183 and through Rotary Valve-2. A desorbent stream, which is composed of paradiethylbenzene, flows through Rotary Valve-1 through conduit 131 to the top of bed 101 of FIG. 3. An extract stream, which comprises a mixture of paraxylene and desorbent, is withdrawn from the top of bed 106 via conduit 136 and through Rotary Valve-1.

At the start of the first step time interval, there are five (5) beds (i.e., beds 101-105) in the desorption zone, eight (8) beds (i.e., beds 106-113) in the purification zone, nine (9) beds (i.e., beds 114-122) in the adsorption zone, and two (2) beds (i.e., beds 123 and 124) in the buffer zone. This zone configuration is referred to in this Example as 5:8:9:2.

This initial zone configuration is maintained for a first subinterval of 0.64 min. of the first step time interval. Then, the extract position is switched one bed downstream (i.e., from the top of bed 106 to the top of bed 107) by taking extract through Rotary Valve-2 via conduit 167. At this point, the zone configuration becomes 6:8:8:2.

After a second subinterval, which ends at 1.27 min. of the first step time interval, the feed position is switched from Rotary Valve-1 to Rotary-2, causing feed to flow into the top of bed 115 (instead of the top of bed 114). This switch results in a new zone configuration of 6:7:10:1.

After a complete step time interval of 1.91 min., the first step is completed. Rotary Valve-1 and Rotary Valve-2 are shifted one position to direct streams to one bed downstream from the positions at the start of the first step, and a second step is started by flowing streams through Rotary Valve-1. At the start of the second step time interval, there are five (5) beds (i.e., beds 102-106) in the desorption zone, eight (8) beds (i.e., beds 107-114) in the purification zone, nine (9) beds (i.e., beds 115-123) in the adsorption zone, and two (2) beds (i.e., beds 124 and 101) in the buffer zone. The zone configurations at the beginning of the first step and the second step are both 5:8:9:2.

The first step is repeated 23 times to complete a cycle of 24 steps, and then the cycle is repeated.

The process of Example 3 results in a paraxylene productivity of 36.15 ton/hr and a total throughput of 157.45 ton/hr, based on the total amount of feed that is fed to the system.

Example 4 (Comparative)

Example 4 uses the same single rotary valve operation as described in Example 2, but increases the desorbent to feed ratio to increase the throughput of the process. In Example 2, the desorbent to feed ratio is 0.97, whereas in Example 4, the desorbent to feed ratio is 1.70.

The composition of the feed is the same as Example 1. As with Example 1, conditions are maintained to obtain paraxylene purity at 99.7% and paraxylene recovery at 97.0%. Each step time interval in Example 4 lasts for 1.91 min. There are no step subintervals in Example 4.

In Example 4, feed is introduced at a rate of 2.67 $m^3$/min. (vs. 2.43 $m^3$/min. in Example 1), desorbent is introduced at a rate of 4.53 $m^3$/min. (vs. 2.43 $m^3$/min in Example 1), extract is withdrawn at a rate of 2.98 $m^3$/min. (vs. 1.61 $m^3$/min in Example 1), and raffinate is withdrawn at a rate of 4.22 $m^3$/min. (vs. 3.26 $m^3$/min in Example 1).

At the start of a first step time interval, the feed stream flows through the rotary valve through conduit 144 to the top of bed 114 of FIG. 3. The raffinate stream, which comprises a mixture of metaxylene, orthoxylene, ethylbenzene, and desorbent, is withdrawn from the top of bed 124 via conduit 154. The desorbent stream, which is composed of paradiethylbenzene, flows through conduit 131 to the top of bed 101 of FIG. 3. The extract stream, which comprises a mixture of paraxylene and desorbent, is withdrawn from the top of bed 106 via conduit 136.

At the start of the first step time interval, there are five (5) beds (i.e., beds 101-105) in the desorption zone, eight (8) beds (i.e., beds 106-113) in the purification zone, ten (10) beds (i.e., beds 114-123) in the adsorption zone, and one (1) bed (i.e., bed 124) in the buffer zone. The zone configuration in Example 2 is 5:8:10:1.

After a complete step time interval of 1.91 min., the first step is completed. The rotary valve is shifted one position to direct streams to one bed downstream from the positions at the start of the first step, and a second step is started by flowing streams through the rotary valve.

The first step is repeated 23 times to complete a cycle of 24 steps, and then the cycle is repeated.

The process of Example 4 results in a paraxylene productivity of 34.86 ton/hr and a total throughput of 151.83 ton/hr, based on the total amount of feed that is fed to the system.

Example 5

This Example describes the use of a dual rotary valve operation of a simulated moving bed process for separating paraxylene from an equilibrium mixture of paraxylene, metaxylene, orthoxylene, and ethylbenzene. The operation uses both Varicol and PowerFeed. The separation takes place in a bed simulated moving bed apparatus as illustrated in FIG. 3. The flow rate of streams is varied over the course of three subintervals during each step time interval.

The composition of the feed is the same as Example 1. As with Example 1, conditions are maintained to obtain paraxylene purity at 99.7% and paraxylene recovery at 97.0%. Each step time interval lasts for 2.17 min There are three step subintervals in Example 5.

In Example 5, feed is introduced at an average rate of 2.50 $m^3$/min. per step (vs. 2.43 $m^3$/min. in Example 1), desorbent is introduced at an average rate of 2.50 $m^3$/min. per step (vs. 2.43 $m^3$/min in Example 1), extract is withdrawn at an rate of 1.75 $m^3$/min. (vs. 1.61 $m^3$/min. in Example 1), and raffinate is withdrawn at an average rate of 3.26 $m^3$/min. per step (vs. 3.26 $m^3$/min in Example 1).

The first rotary valve (Rotary Valve-1) is configured to direct streams one bed upstream from the configuration of the second rotary valve (Rotary Valve-2).

At the start of a first step time interval, the feed stream flows through Rotary Valve-1 through conduit 144 to the top of bed 114 of FIG. 3. The flow rate of the feed stream is 2.81 $m^3$/min.

At the start of the first step time interval, the raffinate stream, which comprises a mixture of metaxylene, orthoxylene, ethylbenzene, and desorbent, is withdrawn from the top of bed 123 via conduit 183 and through Rotary Valve-2. The flow rate of the raffinate stream is 6.58 $m^3$/min.

Also, at the start of the first step time interval, the desorbent stream, which is composed of paradiethylbenzene, flows through Rotary Valve-1 through conduit 131 to the top of bed 101 of FIG. 3. The flow rate of the desorbent stream is 3.77 $m^3$/min.

At the start of the first step time interval, the extract stream, which comprises a mixture of paraxylene and desorbent, is not withdrawn from any bed via any conduit or through Rotary Valve-1 or Rotary Valve-2. In other words, at the beginning of the first step time interval, the flow rate of the extract stream is 0 m³/min.

At the start of the first step time interval, there are zero (0) beds in the desorption zone, thirteen (13) beds (i.e., beds 101-113) in the purification zone, nine (9) beds (i.e., beds 114-122) in the adsorption zone, and two (2) beds (i.e., beds 123 and 124) in the buffer zone. This zone configuration is referred to in this Example as 0:13:9:2.

After a first subinterval of 0.58 min. of the first step time interval, the flow of an extract stream is started, the flow rates of the feed, raffinate, and desorbent streams are changed, and the control of the flow of the feed stream is shifted from Rotary Valve-1 to Rotary Valve-2. At this point, the zone configuration becomes 6:8:8:2.

At the start of the second subinterval of the first step time interval, the feed stream flows through Rotary Valve-2 (instead of Rotary Valve-1) through conduit 175 to the top of bed 115 of FIG. 3. The flow rate of the feed stream is changed from 2.81 m³/min. to 1.98 m³/min.

At the start of the second subinterval of the first step time interval, the raffinate stream continues to be withdrawn from the top of bed 123 via conduit 183 and through Rotary Valve-2. However, the flow rate of the raffinate stream is changed from 6.58 m³/min to 5.79 m³/min.

Also, at the start of the second subinterval of the first step time interval, the desorbent stream continues to flow through Rotary Valve-1 and through conduit 131 to the top of bed 101 of FIG. 3. However, the flow rate of the desorbent stream is changed from 3.77 m³/min. to 5.79 m³/min.

At the start of the second subinterval of the first step time interval, an extract stream is withdrawn from the top of bed 107 via conduit 167 and through Rotary Valve-2.

During the second subinterval of the first step, the flow rate of the extract stream is 1.98 m³/min.

After 1.14 min of the first step time interval, the second subinterval of the first step time interval ends, and the flow rates of the feed, raffinate, desorbent, and extract streams are changed, but no streams are shifted to the other rotary valve. Thus, the zone configuration remains 6:8:8:2.

At the start of the third subinterval of the first step, the feed stream continues to flow through Rotary Valve-2 through conduit 175 to the top of bed 115 of FIG. 3. The flow rate of the feed stream is changed from 1.98 m³/min. to 2.62 m³/min.

At the start of the third subinterval of the first step time interval, the flow of the raffinate stream is discontinued. In other words, the flow rate of the raffinate stream is changed from 5.79 m³/min. to 0 m³/min during the third subinterval.

Also, at the start of the third subinterval of the first step time interval, the flow of the desorbent stream is discontinued. In other words, the flow rate of the desorbent stream is changed from 5.79 m³/min. to 0 m³/min.

At the start of the third subinterval of the first step time interval, the extract stream continues to be withdrawn from the top of bed 107 via conduit 167 and through Rotary Valve-2, but the flow rate of the extract stream is changed from 1.98 m³/min to 2.62 m³/min.

After a complete step time interval of 2.17 min., the first step is completed. Rotary Valve-1 and Rotary Valve-2 are shifted one position to direct streams to one bed downstream from the positions at the start of the first step, and a second step is started by flowing streams through Rotary Valve-1 and Rotary Valve-2 as was done at the start of the first step time interval.

The first step is repeated 23 times to complete a cycle of 24 steps, and then the cycle is repeated.

The process of Example 5 results in a paraxylene productivity of 32.74 ton/hr and a total throughput of 142.61 ton/hr, based on the total amount of feed that is fed to the system.

Results of Examples 1-5 are summarized in Table 1.

TABLE 1

| Example | Number of Rotary Valves | Varicol Operation | PowerFeed Operation | Throughput (Ton/hr) | PX Productivity (Ton/hr) |
| --- | --- | --- | --- | --- | --- |
| 1 | 2 | Yes | No | 138.79 | 31.77 |
| 2 | 1 | No | No | 135.39 | 31.09 |
| 3 | 2 | Yes | No | 157.45 | 36.15 |
| 4 | 1 | No | No | 151.83 | 34.86 |
| 5 | 2 | Yes | Yes | 142.61 | 32.74 |

These results show improved throughput with Varicol operation using two rotary valves. This improvement is obtained without sacrifice of paraxylene productivity. The results of Example 4 show a substantial improvement in both throughput and paraxylene productivity using Varicol operation with a desorbent to feed ratio of greater than 1.5. Furthermore, the results of Example 6 show a substantial improvement, as compared to Example 2, in both throughput and paraxylene productivity using both PowerFeed and Varicol operation.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for separating a product from at least one multicomponent feed by simulated moving bed adsorptive separation, said process comprising:
   (a) directing the flow of a feed stream and a desorbent stream to, and the flow of at least one raffinate stream and an extract stream away from, a plurality of adsorptive beds with a first rotary valve and a second rotary valve, wherein the flow of at least one of the feed stream, desorbent stream, at least one raffinate stream, and extract stream is directed to or away from the adsorptive beds by the first rotary valve at the beginning of a first step time interval; and
   (b) switching the flow of at least one stream to or from the adsorptive beds from the first rotary valve to the second rotary valve after a first subinterval of the first step time interval,
   wherein the first and second rotary valves comprise a plurality of ports in fluid communication with a plurality of conduits in fluid communication with the plurality of adsorptive beds, and wherein the number of adsorptive beds and ports in each rotary valve are equal,
   wherein the relative spacial position of the ports for the feed stream, desorbent stream, at least one raffinate stream, and extract stream in the first rotary valve is the same as the relative spacial position of the corresponding ports for the feed stream, desorbent stream, at least one raffinate stream, and extract stream in the second rotary valve,
   wherein the second rotary valve is positioned so that each stream directed to or from the second rotary valve is one bed away from its corresponding stream directed to or from the first rotary valve.

2. The process of claim 1, further comprising:
(c) discontinuing the flow of the feed stream, desorbent stream, at least one raffinate stream, and extract stream by the first and second rotary valves at the end of the first step time interval;
(d) rotating the first and second rotary valves one position downstream at the end of the first step time interval;
(e) resuming the flow of at least one of the feed stream, desorbent stream, at least one raffinate stream, and extract stream to or from the adsorptive beds by the first rotary valve at the beginning of a second step time interval;
(f) switching the flow of at least one stream to or from the adsorptive beds from the first rotary valve to the second rotary valve after a first subinterval of the second step time interval; and
(g) repeating steps (c)-(f) for a total number of step time intervals equal to the number of adsorptive beds.

3. The process of claim 1, further comprising:
(c') discontinuing the flow of the feed stream, desorbent stream, at least one raffinate stream, and extract stream by the first and second rotary valves at the end of the first step time interval,
(d') rotating the first rotary valve two positions downstream at the end of the first step time interval;
(e') directing the flow of at least one of the feed stream, desorbent stream, at least one raffinate stream, and extract stream to or from the adsorptive beds by the second rotary valve at the beginning of a second time step interval;
(f') switching the flow of at least one stream to or from the adsorptive beds from the second rotary valve to the first rotary valve after a first subinterval of the second step time interval;
(g') discontinuing the flow of the feed stream, desorbent stream, at least one raffinate stream, and extract stream by the first and second rotary valves at the end of the second step time interval,
(h') rotating the second rotary valve two positions downstream at the end of the second step time interval;
(i') directing the flow of at least one of the feed stream, desorbent stream, at least one raffinate stream, and extract stream to or from the adsorptive beds by the first rotary valve at the beginning of a third time step interval;
(j') switching the flow of at least one stream to or from the adsorptive beds from the first rotary valve to the second rotary valve after a first subinterval of the third step time interval; and
(k') repeating steps (c')-(j') for a total number of step time intervals equal to the number of adsorptive beds.

4. The process of claim 1, wherein in step (a), the first rotary valve directs the flow of the feed stream and the desorbent stream to the adsorbent beds, and directs the flow of the extract stream and the at least one raffinate stream from the adsorbent beds, at the beginning of the first step time interval.

5. The process of claim 4, wherein in step (b), the flow of the feed stream to the adsorptive beds is switched from the first rotary valve to the second rotary valve after the first subinterval of the first step time interval.

6. The process of claim 4, wherein in step (b), the flow of the extract stream from the adsorptive beds is switched from the first rotary valve to the second rotary valve after the first subinterval of the first step time interval.

7. The process of claim 6, further comprising:
(b') switching the flow of the raffinate stream from the adsorptive beds from the first rotary valve to the second rotary valve after a second subinterval of the first step time interval, wherein the second subinterval is longer than the first subinterval.

8. The process of claim 7, further comprising:
(b") switching the flow of the feed stream to the adsorptive beds from the first rotary valve to the second rotary valve after a third subinterval of the first step time interval, wherein the third subinterval is longer than the second subinterval.

9. The process of claim 6, further comprising:
(b') switching the flow of the feed stream to the adsorptive beds from the first rotary valve to the second rotary valve after a second subinterval of the first step time interval, wherein the second subinterval is longer than the first subinterval.

10. The process of claim 1, wherein the rate of flow of at least one of the feed stream, the desorbent stream, the at least one raffinate stream, and the extract stream varies during a step time interval.

11. The process of claim 1, wherein the multicomponent feed is a mixture of paraxylene, metaxylene, orthoxylene and ethylbenzene, and wherein the product is paraxylene.

12. A process for separating paraxylene from a mixture of $C_8$ aromatics by simulated moving bed adsorptive separation, the process comprising the steps of:
(a) introducing a feed stream, which comprises $C_8$ aromatics, into a simulated moving bed adsorptive apparatus, wherein the simulated moving bed adsorptive apparatus comprises multiple adsorptive beds containing adsorbent material and a first rotary valve and a second rotary valve, and wherein the feed stream is introduced to the adsorptive beds by the first rotary valve at the beginning of a first step time interval;
(b) introducing a desorbent stream, which comprises desorbent, into the simulated moving bed adsorptive apparatus by the first rotary valve or second rotary valve at the beginning of the first step time interval;
(c) withdrawing an extract stream, which comprises desorbent and paraxylene, from the simulated moving bed adsorptive apparatus by the first rotary valve at the beginning of the first step time interval;
(d) withdrawing at least one raffinate stream, which comprises at least one $C_8$ aromatic, which is different from paraxylene, from the simulated moving bed adsorptive apparatus by the first rotary valve or second rotary valve at the beginning of the first step time interval;
(e) maintaining a flow of circulating fluid throughout the simulated moving bed adsorptive apparatus;
(f) switching the flow of the feed stream, at least one raffinate stream, or extract stream to or from the adsorptive beds from the first rotary valve to the second rotary valve after a first subinterval of the first step time interval;
(g) discontinuing the flow of the feed stream, desorbent stream, at least one raffinate stream, and extract stream by the first and second rotary valves at the end of the first step time interval;
(h) rotating the first and second rotary valves to a bed one position downstream at the end of the first step time interval; and
(i) repeating steps (a)-(h) for a total number of step time intervals equal to the number of adsorptive beds, wherein the first and second rotary valves comprise a plurality of ports in fluid communication with a plurality of conduits in fluid communication with the plurality of adsorptive beds, and wherein the number of adsorptive beds and ports in each rotary valve are equal, wherein the relative spacial position of the ports for the feed stream, desorbent stream, at least one raffinate stream, and extract stream in the first rotary valve is the same as the relative spacial position of the corresponding ports for the feed stream, desorbent stream, at least one raffinate stream, and extract stream in the second rotary valve, and wherein the second rotary valve is positioned so that each stream directed to or from the second rotary valve is one bed away from its corresponding stream directed to or from the first rotary valve.

13. The process of claim 12, further comprising:
(f') switching the flow of one of the streams not switched in step (f) to or from the adsorptive beds from the first rotary valve to the second rotary valve after a second subinterval of the first step time interval.

14. The process of claim 12, wherein in step (f), the flow of the feed stream to the adsorptive beds is switched from the first rotary valve to the second rotary valve after the first subinterval of the first step time interval.

15. The process of claim 12, wherein in step (f), the flow of the extract from the adsorptive beds is switched from the first rotary valve to the second rotary valve after a first subinterval of the first step time interval.

16. The process of claim 15, wherein in step (f'), the flow of the raffinate stream from the adsorptive beds is switched from the first rotary valve to the second rotary valve after a second subinterval of the first step time interval, wherein the second subinterval is longer than the first subinterval.

17. The process of claim 16, further comprising:
(f'') switching the flow of the feed stream to the adsorptive beds from the first rotary valve to the second rotary valve after a third subinterval of the first step time interval, wherein the third subinterval is longer than the second subinterval.

18. The process of claim 15, wherein in step (f'), the flow of the feed stream to the adsorptive beds is switched from the first rotary valve to the second rotary valve after a second subinterval of the first step time interval, wherein the second subinterval is longer than the first subinterval.

19. The process of claim 12, wherein the rate of flow of at least one of the feed stream, the desorbent stream, the at least one raffinate stream, and the extract stream varies during a step time interval.

20. The process of claim 12, wherein the mixture of $C_8$ aromatics is a mixture of paraxylene, metaxylene, orthoxylene and ethylbenzene.

* * * * *